United States Patent [19]

Patel et al.

[11] Patent Number: 5,340,572
[45] Date of Patent: Aug. 23, 1994

[54] ALKALINE OPHTHALMIC SUSPENSIONS

[75] Inventors: Rajesh Patel, San Mateo; Lyle Bowman, Pleasanton; Margarita Vildaver, Napa; Raymond Chen, Union City, all of Calif.

[73] Assignee: Insite Vision Incorporated, Alameda, Calif.

[21] Appl. No.: 14,512

[22] Filed: Feb. 8, 1993

[51] Int. Cl.$^5$ .................. A61K 31/74; A61K 9/14; A61F 2/14
[52] U.S. Cl. .................. 424/78.04; 424/427; 424/428; 424/489; 514/912; 514/913; 514/914
[58] Field of Search .................. 514/912, 913, 914; 424/78.04, 427, 428, 489

[56] References Cited

U.S. PATENT DOCUMENTS

| | | | |
|---|---|---|---|
| 2,798,053 | 7/1957 | Brown | 514/912 |
| 3,947,573 | 3/1976 | Rankin | 424/78.04 |
| 4,039,662 | 8/1977 | Hecht et al. | 514/59 |
| 4,127,674 | 11/1978 | Leopold | 514/166 |
| 4,136,250 | 1/1979 | Mueller et al. | 528/29 |
| 4,192,827 | 3/1980 | Mueller et al. | 525/123 |
| 4,230,724 | 10/1980 | Cooper et al. | 514/570 |
| 4,271,143 | 6/1981 | Schoenwald et al. | 514/9 |
| 4,407,791 | 4/1983 | Stark | 424/78.04 |
| 4,407,792 | 10/1983 | Schoenwald et al. | 514/397 |
| 4,443,432 | 4/1984 | Garabedian et al. | 424/606 |
| 4,461,904 | 7/1984 | York | 548/333.1 |
| 4,474,751 | 10/1984 | Haslam et al. | 514/11 |
| 4,478,818 | 10/1984 | Shell et al. | 424/426 |
| 4,524,063 | 6/1985 | Wheeler | 514/555 |
| 4,548,990 | 10/1985 | Mueller et al. | 525/123 |
| 4,559,343 | 12/1985 | Han et al. | 514/264 |
| 4,615,697 | 10/1986 | Robinson | 424/428 |
| 4,617,186 | 10/1986 | Schafer et al. | 424/78.04 |
| 4,644,007 | 2/1987 | York | 514/392 |
| 4,686,214 | 8/1987 | Boltralik | 514/179 |
| 4,717,725 | 3/1988 | York, Jr. | 514/278 |
| 4,737,492 | 4/1988 | Gerson et al. | 514/204 |
| 4,820,737 | 4/1989 | Schoenwald et al. | 514/654 |
| 4,822,819 | 4/1989 | Desantis et al. | 514/530 |
| 4,888,168 | 12/1989 | Potts et al. | 514/363 |
| 4,911,920 | 3/1990 | Jani et al. | 424/78.04 |
| 5,106,615 | 4/1992 | Dikstein | 424/78.04 |

FOREIGN PATENT DOCUMENTS

| | | |
|---|---|---|
| 81924 | 6/1983 | European Pat. Off. |
| WO83/03544 | 10/1983 | PCT Int'l Appl. |
| WO84/04680 | 12/1984 | PCT Int'l Appl. |
| WO84/04681 | 12/1984 | PCT Int'l Appl. |
| WO87/01943 | 4/1987 | PCT Int'l Appl. |
| WO89/06964 | 8/1989 | PCT Int'l Appl. |
| WO92/00044 | 1/1992 | PCT Int'l Appl. |
| WO92/00707 | 1/1992 | PCT Int'l Appl. |
| 2012634 | 2/1990 | Spain. |
| 2007091 | 5/1979 | United Kingdom. |
| 2013084 | 8/1979 | United Kingdom. |

OTHER PUBLICATIONS

Pharmaceutica Acta Helvetiae, vol. 39, pp. 615 et seq.
Pharmaceutica Acta Helvetiae, vol. 39, pp. 546 et seq (1964).
Canadian Journal of Pharmaceutical Sciences 10, No. 1, 1975, pp. 16–20.
Ophthalmology, vol. 91, No. 1, Oct. 1984, pp. 1199–1204.
Klin. Mbl. Augenheilk 189 (1986), pp. 254–256.
Klin. Mbl. Augenheilk. 189 (1986), pp. 51–54.

*Primary Examiner*—Thurman K. Page
*Assistant Examiner*—Carlos Azpuru
*Attorney, Agent, or Firm*—Howrey & Simon

[57] ABSTRACT

Topical ophthalmic medicament delivery system combining an aqueous ophthalmic gel suspension at a pH equal to or greater than 7.5 and an osmotic pressure of from 10 to about 400 mOsM containing a pharmaceutically effective amount of one or more ophthalmic medicaments of from about 0.05% to about 10% by weight, based on the total weight of the suspension, of a carboxyl-containing polymer prepared by polymerizing one or more carboxyl-containing monoethylenically unsaturated monomers and less then about 5% by weight of a cross-linking agent. The systems have a viscosity of from about 1,000 to about 30,000 centiposes prior to administration to the eye and remain a gel in the eye for a prolonged period of time allowing for the sustained release of one or medicaments such as amine containing antibiotics alone or in combination with cortiscosteroids.

18 Claims, No Drawings

ALKALINE OPHTHALMIC SUSPENSIONS

FIELD OF THE INVENTION

This invention relates to new alkaline polymeric gel suspensions for topical ophthalmic application and to their preparation. More particularly, this invention relates to topical ophthalmic delivery systems for controlled, sustained release of one or more medicaments after administration in reliable drop or ribbon form.

BACKGROUND OF THE INVENTION

In topical administration of medicaments to the eye, a variety of factors can be important. These factors include comfort, consistency and accuracy of dosage, type and time of any vision interference, ease of administration, and timing of delivery. Prior ophthalmic delivery vehicles have suffered drawbacks in one or more of those areas.

For example, eye drops in the form of aqueous solutions or suspensions are typically rapidly washed away by the eye's tear fluid. Ointments or creams blur the vision, and also have comparatively short residence times in the eye. Gelatin lamellae or other films or sheets, ocular inserts and non-aqueous suspensions and emulsions all can cause immediate pain and continuing discomfort and can also interfere with vision.

Consequently, there is a constant search for new and improved methods and systems for the topical administration of medicaments to the eye. In recent years, much attention has been directed to polymeric based topical ophthalmic delivery systems. Some of the polymeric systems have proved useful for various applications. However, few systems, if any, are particularly suitable for all applications. Thus, new systems are continuously being developed.

Schoenwald et al., in U.S. Pat. Nos. 4,271,143 and 4,407,792, issued Jun. 2, 1981 and Oct. 4, 1983, respectively, discloses ophthalmic delivery systems containing an aqueous dispersion of an ophthalmic drug and a high molecular weight polymer. The systems are in the form of a highly viscous, i.e., 40,000 to 300,000 cps, gel having a preferred pH of from about 4.5 to about 8.5. However, at a viscosity of above 30,000 cps, reliable administration in drop form is at best difficult to achieve and at worst impossible. Thus, these systems are difficult to administer so as to provide consistent, accurate dosages and may be uncomfortable to administer as well.

Toko, in UK Patent Application No. GB 2007091A, describes an ophthalmic composition comprising a carboxy vinyl polymer in the form of a gel having a pH of 5 to 8 and a viscosity of 1,000 to 100,000 cps. The relatively low viscosity preparations having viscosities of 1,000 to 10,000 are stated to have good flowability and to be amenable to application by drops directly into the mucous membrane around the eyeball. The preparations having viscosities of from 10,000 to 100,000 cps are stated to be amenable to application to the eyelids like conventional ointments. However, in both higher and lower viscosity situations it is stated that the tears liquify the gel. Consequently, the use of sodium chloride in the preparation is recommended for sustained efficiency because sodium chloride is said to delay breakdown of the gel when the compositions are applied to the mucous membrane of the eye. However, the sodium chloride is also said to convert the gel to a liquid with a great reduction in viscosity. Therefore, when sodium chloride is added to the composition, increased polymer amounts are recommended to compensate for such viscosity reduction due to the addition of sodium chloride.

Although delaying breakdown of a gel of a given viscosity by using the Toko teachings might have some benefits, it is that given viscosity which will influence whether reliable administration in drop form is achievable or whether ointment-like administration, together with its dosage problems, will be dictated. Whether the alleged sustained efficiency benefit said in Toko to be associated with a sodium chloride additive could even be accomplished at viscosities suitable for drop administration is far from clear from Toko. Nevertheless, even if such a benefit could be obtained with a Toko formulation at a viscosity for administration by drops, the fact that the starting viscosity is at a level low enough to even permit administration by drops is itself limiting on the so-called sustained efficiency. Indeed, as stated in the Toko document, when the preparations are applied, the tears liquify the gel. The sodium chloride merely is said to delay that breakdown.

Haslam et al., in U.S. Pat. No. 4,474,751, issued Oct. 2, 1984, discloses an ophthalmic drug delivery system utilizing thermosetting gels. The drug delivery system consists of a clear liquid which forms a semi-solid gel at human body temperatures. The sol-gel transition temperature and rigidity of the gel may be modified by changes in polymer concentration, adjustment of the pH and/or ionic strength of the solution. The polymers used in the delivery system include tetra substituted derivatives of various substituted unsaturated alkyl diamines, such as ethylene diamine and propylene diamine. The substituted diamine systems used are of a pH of from 2 to 9, preferably 4 to 8.

In contrast to the diamine based systems disclosed by Haslam et al., Davis et al., in International Applications WO 89/06964 and WO 92/00044, published under the Patent Cooperation Treaty on Aug. 10, 1989 and Jan. 9, 1992, respectively, discloses new topical medicament delivery systems that are administrable in drop form and, after coming into contact with the eye's tear fluid, rapidly gel in the eye to a substantially greater viscosity than the viscosity of the administered drop.

The Davis et al. topical ophthalmic medicament delivery systems include an aqueous suspension containing from about 0.1% to about 6.5% by weight, based on the total weight of the suspension, of a carboxyl-containing polymer prepared by polymerizing one or more carboxyl-containing monoethylenically unsaturated monomers and less than about 5% by weight of a cross-linking agent. The polymer has an average particle size of not more than about 50 microns in equivalent spherical diameter and are lightly cross-linked such that the suspension is administrable in drop form. The suspensions are at a relatively low pH, i.e., a pH of from 3 to 6.5, prior to administration and undergo increased gellation upon contact with the eye.

Davis et at., in International Application WO 92/00707, published under the Patent Cooperation Treaty on Jan. 23, 1992, discloses another new topical medicament delivery system containing an aqueous ophthalmic gel suspension useful for dry eye applications and administrable to the eye in drop form such that it releases water and one or more ophthalmic vasoconstrictors contained therein. The dry eye delivery systems containing an ophthalmic vasoconstrictor include an aqueous suspension containing from about 0.1% to about 6.5% by weight, based on the total weight of the suspension, of a carboxyl-containing polymer prepared by polymerizing one or more carboxyl-containing monoethylenically unsaturated monomers and less than about 5% by weight of a cross-linking agent. The suspensions have a pH of from about 6.6 to about 8.0.

Although each of the foregoing ophthalmic formulations can be acceptable for some purposes in connection with the delivery of certain ophthalmic medicaments, they can be unacceptable for other purposes. For example, problems of ease and reliability of administration, comfort and/or sustained efficacy can be encountered.

OBJECTS AND SUMMARY OF THE INVENTION

It is an object of this invention to provide new alkaline topical ophthalmic medicament delivery methods and systems (and methods of their preparation) which overcome or minimize problems of the sort previously noted. In particular, it is an object of this invention to provide new alkaline topical ophthalmic medicament delivery systems that are particularly suitable for the administration of medicaments that unexpectedly react with the polymer system.

It is also an object of this invention to provide new topical ophthalmic medicament delivery methods and systems that are easily administrable to the eye in drop form.

A further object of this invention is to provide such new topical ophthalmic medicament delivery methods and systems which employ aqueous suspensions of particular lightly cross-linked polymers of acrylic acid or the like containing an ophthalmic medicament. Such systems having a pH equal to or greater than 7.5, are particularly suitable for the administration of amine containing medicaments, such as certain antibiotics, e.g., tobramycin, which have unexpectedly been found not to be as effectively administered using similar systems at lower pH. Also, such systems are particularly suitable for the delivery of two or more medicaments such as an antibiotic, e.g., tobramycin, and a corticosteroid, e.g., prednisolone, which have heretofore not been as effectively administered using similar systems at lower pH.

Yet another object of this invention is to provide new topical ophthalmic medicament delivery systems that are easily administrable in drop form and, after coming into contact with the eye's tear fluid, remain as a gel in the eye for a prolonged period of time.

Yet another object of this invention is to provide such new topical ophthalmic suspensions that are easily administrable in drop form, and allow for the sustained administration of medicaments that are not as effectively administered in systems having a pH below 7.5.

A still further object of this invention is to provide methods of preparing these new topical ophthalmic medicament delivery systems.

An additional object of this invention is to provide a method of administering various medicaments to and treating various conditions of the eye with the new topical ophthalmic suspensions.

In accordance with a preferred form of the invention intended to accomplish at least some of the foregoing objects, a sustained release topical ophthalmic medicament delivery system comprises an aqueous suspension at a pH equal to or greater than 7.5, preferably equal to or greater than about 8.0, and more preferably between about 8.4 and about 9.3, and having an osmotic pressure of from about 10 to about 400 mOsM containing from about 0.05% to about 10% by weight, based on the total weight of the suspension, of a lightly cross-linked carboxyl-containing polymer prepared by polymerizing one or more carboxyl-containing monoethylenically unsaturated monomers and less than about 5% by weight of a cross-linking agent, such weight percentages of monomers being based on the total weight of monomers polymerized. The suspension has a viscosity of from about 1,000 to about 100,000 centipoises prior to administration to the eye and is administrable to the eye in drop or ribbon form. Preferably the viscosity is from about 5,000 to in about 30,000 centipoises more preferably about 5,000 to about 15,000 centipoises, and is administrable to the eye in drop form. The polymer has an average particle size of not more than about 50 μm, preferably not more than about 30 μm, in equivalent spherical diameter. Upon contact of the suspension with tear fluid of the eye, the suspension remains a gel for a prolonged period of time. The contact over a prolonged period of time provides comfortable and sustained release of either one or more medicaments which otherwise may not be so easily administered. The polymer is preferably prepared from at least about 50% by weight, more preferably at least about 90% by weight, of one or more carboxyl-containing monoethylenically unsaturated monomers. Desirably the polymer is prepared by suspension or emulsion polymerizing acrylic acid and a non-polyalkenyl polyether difunctional cross-linking agent to a particle size of not more than about 50 μm, preferably not more than about 30 μm, in equivalent spherical diameter. A preferred cross-linking agent is divinyl glycol. It may be desirable to replace up to about 40% by weight of the carboxyl-containing monoethylenically unsaturated monomers by one or more non-carboxyl-containing monoethylenically unsaturated monomers containing only physiologically and ophthalmologically innocuous substituents.

The osmotic pressure is preferably achieved by using a physiologically and ophthalmologically acceptable salt in an amount of from about 0.01% to about 1% by weight, based on the total weight of the suspensions. A preferred salt is sodium chloride.

The suspension includes a pharmaceutically effective amount of one or more ophthalmic medicaments, at least one of the medicaments having multiple amine groups. The medicaments may be present in desired amount, preferably 0.005% to about 10% by weight, based on the total weight of the suspension. Preferred medicaments include amine containing antibiotics or a combination of amine containing antibiotics and one or more corticosteroids.

In preferred embodiments of the invention an antibiotic is selected for use in the sustained release topical ophthalmic medicament delivery system, wherein the antibiotic is selected from the group consisting of emilorde, tetracycline, chlortetracycline, bacitracin, amikackin, neomycin, polymycin, polymycin B, gramicidin, oxytetracycline, chloramphenicol, gentamycin, penicillins, erythromycin, sulfacetamide, tobramycin, trospectomycin, vancomycin, enoracin and clindamycin. Tobramycin is particularly preferred.

In some aspects of the invention it is preferred to additionally use an antiinflammatory agent, preferably selected from the group consisting of ibuprofen, diclofenac, flurbiprofen, napoxen, esters of ibuprofen, naproxen, ketorolac, suprofen, interferons and I11-ra.

When corticosteroids are employed preferred corticosteroids are selected from the group consisting of fluorometholone, dexamethasone, hydrocortisone, fluorocinolone, medrysone, prednisolone, prednisolone acetate, and methylprednisolone. Prednisolone acetate is particularly preferred.

In contrast to other systems, the present invention provides an ophthalmic delivery system that not only has the benefits of administration in drop form, but also does not suffer from breakdown limitations due to administration at a viscosity suitable for drops. Because the particles are present in a suspension, the degree of cross-linking is necessarily at a level such as to have avoided substantial dissolution of the polymer. On the other hand, since gelation is desired, the degree of cross-linking is necessarily not so great that gelation is precluded. Moreover, if the polymer particle size is too large, induced swelling can tend to take up voids in the volume between large particles that are in contact with one another, rather than the swelling tending to cause gelation.

In the most preferred forms of the invention, the particles are not only subject to the upper size limits described above, but also to a narrow particle size distribution. Such use of a monodispersion of particles, which aids in good particle packing, yields a maximum increased viscosity upon contact of the suspension with the tears and increases eye residence time. At least about 80%, more preferably at least about 90% and most preferably at least about 95%, of the particles should be within a no more than about 10 $\mu$m band of major particle size distribution, and overall, i.e., considering particles both within and outside such band there should be no more than about 20%, preferably no more than about 10% and most preferably no more than about 5% fines, i.e., particles of a size below 1 $\mu$m. It is also preferred that as the average particle size is lowered from the upper limit of 50 $\mu$m, more preferably 30 $\mu$m, to lower sizes such as 6 $\mu$m, that the band of major particle size distribution be also narrowed, for example to 5 $\mu$m. Preferred sizes for particles within the band of major particle distribution are less than about 30 $\mu$m, more preferably less than about 20 $\mu$m, most preferably from about 1 $\mu$m to about 5 $\mu$m.

The foregoing and other aspects, objects and advantages of the present invention, as well as its nature, scope and utilization, will become more apparent to those skilled in the art from the following detailed description and the appended claims.

DETAILED DESCRIPTION OF THE INVENTION

The lightly cross-linked polymers of acrylic acid or the like used in practicing this invention are, in general, well known in the art. In a preferred embodiment such polymers are ones prepared from at least about 90% and preferably from about 95% to about 99.9% by weight, based on the total weight of monomers present, of one or more carboxyl-containing monoethylenically unsaturated monomers. Acrylic acid is the preferred carboxyl-containing monoethylenically unsaturated monomer, but other unsaturated, polymerizable carboxyl-containing monomers, such as methacrylic acid, ethacrylic acid, $\beta$-methylacrylic acid (crotonic acid), cis-$\alpha$-methylcrotonic acid (angelic acid), trans-$\beta$-methylcrotonic acid (tiglic acid), $\alpha$-butylcrotonic acid, $\alpha$-phenylacrylic acid, $\alpha$-benzylacrylic acid, $\alpha$-cyclohexylacrylic acid, $\beta$-phenylacrylic acid (cinnamic acid), coumaric acid (o-hydroxycinnamic acid), umbellic acid (p-hydroxycoumaric acid), and the like can be used in addition to or instead of acrylic acid.

Such polymers are cross-linked by using a small percentage, i.e., less than about 5%, such as from about 0.01% or from about 0.1% to about 5%, and preferably from about 0.2% to about 2%, based on the total weight of monomers present, of a polyfunctional cross-linking agent. Included among such cross-linking agents are non-polyalkenyl polyether difunctional cross-linking monomers such as divinyl glycol; 2,3-dihydroxyhexa-1,5-diene; 2,5-dimethyl-1,5-hexadiene; divinylbenzene; N,N-diallylacrylamide; N,N-diallylmethacrylamide and the like. Also included are polyalkenyl polyether cross-linking agents containing two or more alkenyl ether groupings per molecule, preferably alkenyl ether groupings containing terminal H$_2$C=C< groups, prepared by etherifying a polyhydric alcohol containing at least four carbon atoms and at least three hydroxyl groups with an alkenyl halide such as allyl bromide or the like, e.g., polyallyl sucrose, polyallyl pentaerythritol, or the like; see, e.g., Brown U.S. Pat. No. 2,798,053. Diolefinic non-hydrophilic macromeric cross-linking agents having molecular weights of from about 400 to about 8,000, such as insoluble di- and polyacrylates and methacrylates of diols and polyols, diisocyanate-hydroxyalkyl acrylate or methacrylate reaction products, and reaction products of isocyanate terminated prepolymers derived from polyester diols, polyether diols or polysiloxane diols with hydroxyalkylmethacrylates, and the like, can also be used as the cross-linking agents; see, e.g., Mueller et al. U.S. Pat. Nos. 4,192,827 and 4,136,250.

The lightly cross-linked polymers can of course be made from a carboxyl-containing monomer or monomers as the sole monoethylenically unsaturated monomer present, together with a cross-linking agent or agents. They can also be polymers in which up to about 40%, and preferably from about 0% to about 20% by weight, of the carboxyl-containing monoethylenically unsaturated monomer or monomers has been replaced by one or more non-carboxyl-containing monoethylenically unsaturated monomers containing only physiologically and ophthalmologically innocuous substituents, including acrylic and methacrylic acid esters such as methyl methacrylate, ethyl acrylate, butyl acrylate, 2-ethylhexylacrylate, octyl methacrylate, 2-hydroxyethyl-methacrylate, 3-hydroxypropylacrylate, and the like, vinyl acetate, N-vinylpyrrolidone, and the like; see Mueller et at. U.S. Pat. No. 4,548,990 for a more extensive listing of such additional monoethylenically unsaturated monomers. Particularly preferred polymers are lightly cross-linked acrylic acid polymers wherein the cross-linking monomer is 2,3-dihydroxyhexa-1,5-diene or 2,3-dimethylhexa-1,5-diene.

The lightly cross-linked polymers used in practicing this invention are preferably prepared by suspension or emulsion polymerizing the monomers, using conventional free radical polymerization catalysts, to a dry particle size of not more than about 50 $\mu$m in equivalent spherical diameter; e.g., to provide dry polymer particles ranging in size from about 1 to about 30 $\mu$m, and preferably from about 3 to about 20 $\mu$m, in equivalent spherical diameter. In general, such polymers will range in molecular weight estimated to be about 2,000,000 to about 4,000,000, although some polymers may be of higher molecular weight.

Aqueous suspensions containing polymer particles prepared by suspension or emulsion polymerization whose average dry particle size is appreciably larger than about 50 μm in equivalent spherical diameter are less comfortable when administered to the eye than suspensions otherwise identical in composition containing polymer particles whose equivalent spherical diameters are, on the average, below about 50 μm. Moreover, above the average 50 μsize, the advantage of substantially increased viscosity after administration is not realized. It has also been discovered that lightly cross-linked polymers of acrylic acid or the like prepared to a dry particle size appreciably larger than about 50 μm in equivalent spherical diameter and then reduced in size, e.g., by mechanically milling or grinding, to a dry particle size of not more than about 50 μm in equivalent spherical diameter do not work as well as polymers made from aqueous suspensions. While we do not wish to be bound by any theory or mechanism advanced to explain the functioning of this invention, one possible explanation for the difference of such mechanically milled or ground polymer particles as the sole particulate polymer present is that grinding disrupts the spatial geometry or configuration of the larger than 50 μm lightly cross-linked polymer particles, perhaps by removing uncross-linked branches from polymer chains, by producing particles having sharp edges or protrusions, or by producing ordinarily too broad a range of particle sizes to afford satisfactory delivery system performance. In any event, such mechanically reduced particles are less easily hydrated in aqueous suspension than particles prepared to the appropriate size by suspension or emulsion polymerization, and are less comfortable once gelled than gels produced using the aqueous suspensions of this invention. However, up to about, 40% by weight, e.g., from about 0% to over 20% by weight, based on the total weight of lightly cross-linked particles present, of such milled or ground polymer particles can be admixed with solution or emulsion polymerized polymer particles having dry particle diameters of not more than about 50 μm when practicing this invention. Such mixtures will also provide satisfactory viscosity levels in the ophthalmic medicament delivery systems with ease and comfort of administration and satisfactory sustained release of the medicament to the eye, particularly when such milled or ground polymer particles, in dry form, average from about 0.01 to about 30 μm, and preferably from about 1 to about 5 μm, in equivalent spherical diameter.

In the most preferred embodiment of the invention, the particles have a narrow particle size distribution within a 10 μm band of major particle size distribution which contains at least 80%, more preferably at least 90%, most preferably at least 95% of the particles. Also, there is no more than 20%, preferably no more than 10%, and most preferably no more than 5% particles of a size below 1 μm. Apart from that, the use of a monodispersion of particles will give maximum viscosity and an increased eye residence time of the ophthalmic medicament delivery systems for a given particle size. Monodisperse particles having a particle size of 30 μm and below are most preferred. Good particle packing is aided by a narrow particle size distribution.

The aqueous suspensions of this invention will contain amounts of lightly cross-linked polymer particles ranging from about 0.05% to about 10% by weight, and preferably from about 0.5 to about 6.5 and more preferably about 0.1% to about 4.5% by weight, based on the total weight of the aqueous suspension. They will preferably be prepared using pure, sterile water, preferably deionized or distilled, having no physiologically or ophthalmologically harmful constituents, and will be adjusted to a pH of about 7.5 or above preferably 8.0 or above, and more preferably from about 8.4 to about 9.3, using any physiologically and ophthalmologically acceptable pH adjusting acids, bases or buffers, e.g., acids such as acetic, boric, citric, lactic, phosphoric, hydrochloric, or the like, bases such as sodium hydroxide, sodium phosphate, sodium borate, sodium titrate, sodium acetate, sodium lactate, THAM (trishydroxymethylaminomethane), or the like and salts and buffers such as citrate/dextrose, sodium bicarbonate, ammonium chloride and mixtures of the aforementioned acids and bases. A pH above 9.3 is ordinarily undesirable for material placed in the eye because tissues in the eye may be harmed or unacceptable discomfort may occur.

When formulating the aqueous suspensions of this invention, their osmotic pressure ($\pi$) will be adjusted to from about 10 mOsM to about 400 mOsM, and preferably from about 100 to about 250 mOsM, using appropriate amounts of physiologically and ophthalmologically acceptable salts. Sodium chloride is preferred to approximate physiologic fluid, and amounts of sodium chloride ranging from about 0.01% to about 1% by weight, and preferably from about 0.05% to about 5.0% by weight, based on the total weight of the aqueous suspension, will give osmolalities within the above-stated ranges. Equivalent amounts of one or more salts made up of cations such as potassium, ammonium and the like and anions such as chloride, citrate, ascorbate, borate, phosphate, bicarbonate, sulfate, thiosulfate, bisulfite and the like, e.g., potassium chloride, sodium thiosulfate, sodium metabiosulfite, sodium bisulfite, ammonium sulfate, and the like can also be used in addition to or instead of sodium chloride to achieve osmolalities within the above-stated ranges.

The amounts of lightly cross-linked polymer particles, the pH, and the osmotic pressure chosen from within the above-stated ranges will be correlated with each other and with the degree of cross-linking to give aqueous suspensions having viscosities ranging from about 1,000 to about 30,000 centipoise, preferably from about 5,000 to about 30,000 centipoise and more preferably from about 5,000 to about 15,000 centipoise, as measured at room temperature (about 25° C.) using a Brookfield Digital LV-CP Viscometer equipped with a number 52 spindle and at 1.5 rpm.

The medicaments contained in the drug delivery systems of the present invention may be released from the gels at rates that depend on such factors as the drug itself and its physical form, the extent of drug loading and the pH of the system, as well as on any drug delivery adjuvants, such as ion exchange resins compatible with the ocular surface, which may also be present.

Medicaments—substances used in treating or ameliorating a disease or medical condition—including drugs intended to treat therapeutically the eye itself or the tissues surrounding the eye and drugs administered via the ophthalmic route to treat therapeutically a local condition other than one involving the eye, will typically be incorporated in the topical delivery systems of this invention in therapeutically active amounts comparable to amounts administered in other dosage forms, usually in amounts ranging from about 0.005% to about 10% by weight, and preferably from about 0.01% to about 5% by weight, based on the total weight of the formulation.

An illustrative but by no means exhaustive listing of such medicaments includes demulcents (for relief of "dry eye"), antibiotics, antivirals, steroids, amino-substituted steroids, including anti-inflammatory agents, peptides, polypeptides, cardiotonics, antihypertensives, antiallergics, alpha- and beta- adrenergic blocking agents, carbonic anhydrase inhibitors, ophthalmic medicaments such as anticataract agents, antiglaucoma agents and ophthalmic anti-inflammatory agents, ophthalmic lubricating agents, ophthalmic topical or regional anesthetic agents, etc. Specific medicaments that may be used in the present invention include drugs such as amiloride, tetracycline, chlortetracycline, bacitracin, amilsacin, neomycin, polymyxin, polymyxin B, gramicidin, oxytetracycline, chloramphenicol, gentamycin, penicillins, erythromycin, sulfacetamide, tobramycin, trospectomycin, vancomycin, enoxacin, clindamycin, isoflurophate, fluorometholone, dexamethasone, hydrocortisone, fluorocinolone, medrysone, prednisolone, prednisolone acetate, methylprednisolone, fluticasone propionate, betamethasone, triamcinolone, estradiol, ibuprofen, flurbiprofen, naproxen, esters of ibuprofen, flurbiprofen, and naproxen, ketorolac, suprofen, cromolyn, acetazolamide, apraclonidine, or antiinflamatory polypeptides or proteins such as interferons, IL1-ra, and the nontoxic, pharmaceutically acceptable salts thereof. Pro-drug counterparts are also within the scope of the present invention.

The term "pharmaceutically acceptable salt" refers to those salts of the parent compound that do not significantly or adversely affect the pharmaceutical properties (e.g., toxicity, efficacy, etc.) of the parent compound. Pharmaceutically acceptable salts administrable by means of the aqueous suspensions of this invention include, for example, chloride, iodide, bromide, hydrochloride, acetate, nitrate, stearate, pamoate, phosphate and sulfate salts. It is sometimes desirable to use an appropriate salt form of the medicament that increases the water solubility or polar characteristics of the free drug.

The medicament used in the present invention or, if more than one medicament is used then at least one medicament used, has multiple (more than one) amine groups which interact with the polymer used. Accordingly, while the present invention contemplates, in certain cases, use of each of the above medicaments the present invention contemplates in all cases use of those medicaments that substantially interact with the polymer at a pH below about 7.5 but do not substantially react (or cross-link) with the polymer at a pH above about 7.5. While not wishing to be bound by theory, it is believed that certain medicaments have groups that are subject to protonization at low pH, i.e., pH below about 7.5 or 8.0 or 8.4. When protonated, these groups interact with dissociated carboxylic acid and physically bond the medicament to the polymer so that the medicament does not release. Such medicaments include amine containing antibiotics which may interact such as, for example, tetracycline, chlortetracycline, bacitracin, neomycin, polymycin, polymycin B, gramicidin, oxytetracycline, gentamycin, penicillins, sulfacetamide, tobramycin, trospectomycin, vancomycin, ciprofloxacin, olfloxacin, and enoxacin. Of course, other such medicaments may be found to interact with such polymers at a pH below 7.5 or 8.0 or 8.4.

Again, while not wishing to be bound by theory, it is believed that the amine containing medicaments at low pH, interact (or cross-link) with the polymer making up the suspension. At low pH, it is believed that the amine groups are protonated to become $NH_3^+$ groups. The $NH_3^+$ groups then interact with dissociated carboxylic acid and physically bond (or cross-link) to the cross-linked polymer. This phenomenon is observed with drugs having more than one amine group. Consequently, the amine containing medicament is not completely available for release. Under more alkaline conditions, i.e., particularly a pH of about 7.5 and above, preferably 8.0 and above, and more preferably between about 8.4 and about 9.3, the multiple amine groups, for the most part, do not become protonated. Thus, the amine containing medicament does not interact and bind to the polymer. Consequently, substantially all of the medicament is available for release.

As a result of using the suspension of the present invention at an alkaline pH, particularly a pH of 8.0 or 8.4 or above, multiple amine-containing antibiotics unexpectedly exhibit enhanced sustained delivery over longer periods of time when compared to the same polymer systems used at a lower pH.

Moreover, it has unexpectedly been discovered that the delivery systems of the present invention are preferred over the delivery systems heretofore known as the systems of the present invention allow for the controlled delivery of two or more medicaments. For example, it has unexpectedly been found that the above described amine containing medicaments may be beneficially administered along with corticosteroids in sustained controlled amounts from the same suspension over prolonged periods of time. A preferred combination of an amine containing antibiotic and a corticosteroid is the combination of tobramycin and prednisolone acetate. Other preferred corticosteroids include fluorometholone, dexamethasone, hydrocortisone, fluorocinolone, medrysone, prednisolone and methylprednisolone.

The aqueous suspension topical ophthalmic medicament delivery systems of this invention can be formulated in any of several ways. For example, the medicament, the lightly cross-linked polymer particles, and the osmolality-adjusting salt can be preblended in dry form, added to all or part of the water, and stirred vigorously until apparent polymer dispersion is complete, as evidenced by the absence of visible polymer aggregates. Sufficient pH adjusting agent is then added incrementally to reach the desired pH, and more water to reach 100 percent formula weight can be added at this time, if necessary. Another convenient method involves adding the drug to about 95 percent of the final water volume and stirring for a sufficient time to saturate the solution. Solution saturation can be determined in known manner, e.g., using a spectrophotometer. The lightly cross-linked polymer particles and the osmolality-adjusting salt are first blended in dry form and then added to the drug-saturated suspension and stirred until apparent polymer hydration is complete. Following the incremental addition of sufficient pH adjusting agent to reach the desired pH, the remainder of the water is added, with stirring, to bring the suspension to 100 percent formula weight.

These aqueous suspensions can be packaged in preservative-free, single-dose non-reclosable containers. This permits a single dose of the medicament to be delivered to the eye one drop at a time, with the container then being discarded after use. Such containers eliminate the potential for preservative-related irritation and sensitization of the corneal epithelium, as has been observed to occur particularly from ophthalmic medicaments containing mercurial preservatives. Multiple-dose containers can also be used, if desired, particularly since the relatively low viscosities of the aqueous suspensions of this invention permit constant, accurate dosages to be administered dropwise to the eye as many times each day as necessary. In those suspensions where preservatives are to be included, suitable preservatives are chlorobutanol, Polyquat, benzalkonium chloride, cetyl bromide, and the like.

In order that those skilled in the art can more fully appreciate aspects of this invention, the following examples are set forth. These examples are given solely for purposes of illustration, and should not be considered as expressing limitations unless so set forth in the appended claims.

EXAMPLE 1

A hydrated polymeric dispersion is prepared by slowly dispersing 1.0 gram of Novcon ™ AA-1 type polymer into a beaker fitted with an overhead stirrer containing deionized water and stirring for one hour. Then, 0.10 grams of edetate disodium are added to the dispersion followed by stirring for 10 minutes. 0.05 grams of sodium sulfate are then added to the dispersion followed by stirring for 10 minutes. Then, 1.5 grams of sodium borate are added to the dispersion followed by stirring for 30 minutes. The gel is sterilized at 121° C. for 20 minutes. The pH of the gel is adjusted from about 7.5 to about 8.0 by adding 10N sodium hydroxide. Separately, 0.33 grams of tobramycin is dissolved in deionized water. Slowly, the tobramycin solution is added to the gel and stirred for 20 minutes, after rinsing the vial containing the tobramycin solution with deionized water and adding the rinse water to the gel. The final formulation batch size is 100 grams adjusted with water. The pH of the resulting gel is about 8.2. The pH is adjusted to 8.7 by adding 10N sodium hydroxide. All components after sterilization are added by sterile filtration.

Table 1 sets forth the amount of each component in the formulation. Table 2 sets forth various properties of the formulation.

TABLE 1

| Ingredient | Amount of Each Component in Formulation Weight Percent (% w/w) |
| --- | --- |
| Tobramycin, USP | 0.33 |
| Noveon ™ AA-1 | 1.00 |
| Disodium edetate, USP | 0.10 |
| Sodium borate, USP | 1.50 |
| Sodium sulfate, USP | 0.05 |
| Deionized water, q.s. | 100.00 |

TABLE 2

| Parameter | Properties of Formulation |
| --- | --- |
| Appearance | viscous gel |
| Color | colorless |
| Clarity | translucent |
| pH | 8.7 |
| Viscosity | 9750 cps[1/] |
| Osmolarity | 223 mOsM/kg |

[1/]LV-CP-52 1.5 rpm, 0.7 ml sample.

EXAMPLE 2

Hydrated hydroxyethyl cellulose is prepared by adding 0.2 grams of hydroxyethyl cellulose to deionized water in a 600 ml beaker fitted with an overhead stirrer and stirring the mixture overnight. The next day, 1.0 gram of Novcon ™ type polymer is slowly dispersed into the mixture containing the hydroxyethyl cellulose and stirred for 1 hour. Then, 0.1 grams of edetate disodium is added to the mixture followed by stirring for 10 minutes. Then, 0.10 grams of sodium bisulfite is added to the dispersion followed by stirring for 10 minutes, and 0.05 grams of sodium sulfate are added to the dispersion followed by stirring for 10 minutes. The product thus formed is a gel. A dispersion is then prepared by dispersing 0.60 grams of prednisolone acetate in part of the gel using a homogenizer for about one and a half hours. The homogenizer is rinsed with deionized water and the rinse water is added to the dispersion. Subsequently, the gel and dispersion are mixed in a 400 ml beaker, fitted with an overhead stirrer and stirred for 20 minutes. Then, 1.5 grams of sodium borate are added to the mixture and stirred for 30 minutes. The product had a pH of about 6.14. This product is sterilized at 121° C. for 20 minutes, and brought to room temperature. Then, the pH of the gel is brought up to 8.0 by adding 10N sodium hydroxide. Separately, a solution is prepared by dissolving 0.33 grams of tobramycin in deionized water. Then, the solution is added to the gel by sterile filtering through a 0.2 micron filter. The vial is rinsed with deionized water and also added. Then, the product is stirred for 20 minutes and the pH is adjusted to 8.7 by adding 10N sodium hydroxide. The final batch size of the formulation is 100 grams adjusted with water. All additives are added through a sterile filter.

Table 3 sets forth the amount of each component in the formulation. Table 4 sets forth various properties of the formulation.

TABLE 3

| Ingredient | Amount of Each Component in Formulation (% w/w) |
| --- | --- |
| prednisolone acetate, USP | 0.60 |
| tobramycin, USP | 0.33 |
| hydroxyethyl cellulose, NF | 0.20 |
| Noveon ™ AA-1 | 1.00 |
| disodium edetate, USP | 0.10 |
| sodium bisulfite, USP | 0.10 |
| sodium borate, USP | 1.50 |
| sodium sulfate, USP | 0.05 |
| deionized water, q.s. | 100.00 |

TABLE 4

| Parameter | Properties of Products |
| --- | --- |
| Appearance | viscous gel |
| Color | milky white |
| Clarity | opaque |
| pH | 8.7 |
| Viscosity | 11,800 cpm[2/] |
| Osmolarity | 245 mOsM/kg |
| Particle Size Distribution | <5 μm 96% |
|  | <10 μm 100% |

[2/]LV-CP-52 1.5 rpm, 0.7 ml sample.

EXAMPLE 3

A hydrated polymeric gel is prepared by slowly dispersing 1.0 gram of Noveon ™ AA-1 type polymer into a beaker fitted with an overhead stirrer containing deionized water and stirring for one hour. Then, 0.1 grams of edetate disodium are added to the gel followed by stirring for 10 minutes. Then, 0.05 grams of sodium sulfate are added to the gel followed by stirring for 10 minutes. Then, 1.5 grams of sodium borate are added to the gel followed by stirring for 30 minutes. Subsequently, 1.0 gram prednisolone acetate is dispersed in the gel over a period of 30 minutes. The suspension is sterilized at 121° C. for 20 minutes. Then the pH is adjusted to 8.0 by adding 10N sodium hydxide. Separately, 0.33 grams of tobramycin is dissolved in deionized water. Slowly, the tobramycin is added to the gel and stirred for 20 minutes. After rinsing the vial containing the tobramycin solution with deionized water and adding the rinse water to the gel. The final pH is adjusted to about 8.7 by adding 10N sodium hydroxide. The final formulation batch size is 100 grams adjusted with water. The final additions after sterilization are made through a sterile filter.

EXAMPLE 4

A hydrated polymeric gel is prepared by slowly dispersing 1.0 gram of Noveon TM AA-1 type polymer into a beaker fitted with an overhead stirrer containing deionized water and stirring for one hour. Then, 0.2 grams Tyloxapol TM are dissolved in deionized water, added to the gel, and stirred for 10 minutes. Subsequently, 1.0 gram prednisolone acetate is dispersed in part of the gel over a period of 1.5 hours. The gel containing the prednisolone acetate was added to the remaining gel and stirred for 20 minutes. Then, 0.10 grams disodium edetate are added to the gel followed by stirring for 10 minutes. Then, 0.25 grams of sodium chloride are added to the gel followed by stirring for 10 minutes. Then, 0.25 grams of sodium sulfate are added to the gel followed by stirring for 10 minutes. Then, 0.5 grams sodium borate are added to the gel followed by stirring for 30 minutes. Subsequently, the formulation is sterilized at 121° C. for 15 minutes and the pH is adjusted to 8.0 by adding 10N sodium hydroxide. Separately, 0.33 grams of tobramycin is dissolved in deionized water. The tobramycin solution is added to the gel by filtering through a sterile filter (0.2 microns) and stirred for 20 minutes. The pH is adjusted to 8.9 by adding 10N sodium hydroxide. The final formulation batch size is 100 grams adjusted with water. All additions are made with a sterile filter after the sterilization.

The amount of each component in the formulations of Examples 3–4 is set forth in Table 5.

TABLE 5

Amount of Each Component in Formulation

| Formulation | Ex. 3 (% w/w) | Ex. 4 (% w/w) |
| --- | --- | --- |
| Noveon AA-1 | 1.00 | 100 |
| Tyloxapol | — | 0.20 |
| Disodium Edetate | 0.10 | 0.10 |
| Sodium Sulfate | 0.05 | 0.25 |
| Sodium Chloride | — | 0.25 |
| Sodium Borate | 1.50 | 0.50 |
| Prednisolone Acetate | 1.00 | 1.00 |
| Tobramycin | 0.33 | 0.33 |
| Deionized Water, q.s. | 100.0 | 100.00 |

EXAMPLE 5

A hydrated polymeric gel is prepared by slowly dispersing 1.0 gram of Noveon AA-1 type polymer into a beaker fitted with an overhead stirrer containing deionized water and stirring for 1 hour. Then, 0.2 grams Tyloxapol TM are dissolved in deionized water, added to the gel and stirred for 10 minutes. Subsequently, 0.1 grams disodium edetate are added to the gel followed by stirring for 10 minutes. Subsequently, 0.05 grams of sodium sulfate is added to the gel followed by stirring for 20 minutes. Subsequently, 0.1 gram of dexamethasone are added to the gel over a period of 1.5 hours. Then, 1.5 grams sodium borate are added to the gel followed by stirring for 30 minutes. The formulation is sterilized at 121° C. for 20 minutes. The pH is adjusted to 8.0 by adding 10N sodium hydroxide. Separately, 0.33 grams of tobramycin are dissolved in deionized water, added to the gel and stirred for 20 minutes. Then, the pH is adjusted to 8.7 by adding 10N sodium hydroxide. The final formulation is adjusted to 100 grams with water and all additives are added by sterile filtration.

The amount of each component in the formulation of Example 5 is set forth in Table 6.

TABLE 6

Amount of Each Component in Formulation

| Formulation | Ex. 5 (% w/w) |
| --- | --- |
| Noveon AA-1 | 1.00 |
| Tyloxapol | 0.20 |
| Disodium Edetate | 0.10 |
| Sodium Sulfate | 0.05 |
| Sodium Borate | 1.50 |
| Dexamethasone | 0.10 |
| Tobramycin | 0.33 |
| Deionized Water, q.s. | 100.00 |

EXAMPLES 6–8

Different levels of hydroxypropyl methylcellulose (HPMC) are incorporated into the formulation to coat the particles of the prednisolone acetate to form a protective hydration layer around each suspended particle. The formulations are prepared by fitting a beaker with an overhead stirrer and adding a portion of deionized water. Then, slowly adding the HPMC, if listed, and stirring for 1 hour. Then, the Noveon AA-1 type polymer is added and stirred for another hour. Then, Tyloxapol TM, a surfactant, is added to the gel after dissolving in water and then stirred for 10 minutes. Prednisolone acetate is then added to the gel and stirred for 20 minutes. The disodium edetate, sodium sulfate and sodium borate are then added in sequence with 10 minutes, 10 minutes and 30 minutes of stirring, respectively. Subsequently, the gel is sterilized at 121° C. for 20 minutes and brought to room temperature. The pH of the gel is adjusted to 8.0 by adding 10N sodium hydroxide. Separately, tobramycin is added to the gel after dissolving in water. The tobramycin solution is added by sterile filtering through a 0.2 micron filter. The gel is then stirred for 20 minutes and the pH is adjusted by adding 10N sodium hydroxide. The final formulation batch size is 300 grams adjusted with water.

The amount of each component and properties of each formulation of Examples 6–8 is listed in Table 7.

TABLE 7

Amount of Each Component and Properties of Each Formulation of Examples 6–8

| INGREDIENTS | FORMULATION | | |
| --- | --- | --- | --- |
| | Ex. 6 % w/w | Ex. 7 % w/w | Ex. 8 % w/w |
| Noveon TM AA-1 | 1.00 | 1.00 | 1.00 |

TABLE 7-continued

Amount of Each Component and Properties of Each Formulation of Examples 6-8

| INGREDIENTS | FORMULATION | | |
|---|---|---|---|
| | Ex. 6 % w/w | Ex. 7 % w/w | Ex. 8 % w/w |
| Hydroxypropyl Methylcellulose | — | 1.00 | 0.20 |
| Disodium Edetate USP | 0.10 | 0.10 | 0.10 |
| Sodium Sulfate, USP | 0.05 | 0.25 | 0.05 |
| Sodium Borate, NF | 1.50 | 0.50 | 1.50 |
| Sodium Chloride, USP | — | 0.25 | — |
| Tyloxapol | 0.2 | 0.2 | 0.2 |
| Tobramycin, USP | 0.33 | 0.33 | 0.33 |
| Prednisolone Acetate, USP | 0.60 | 0.60 | 0.60 |
| D.I. Water, q.s. | 100.00 | 100.00 | 100.00 |
| pH | 8.7 | 8.8 | 8.7 |
| Osm., mOsm/Kg | 218 | 292 | 218 |
| Viscosity, (CP-52, 1.5 rpm) cps | 8,220 | 17700 | 10700 |
| Batch Size, gm | 300 | 300 | 300 |
| Sterile | Yes | Yes | Yes |
| Appearance | thick viscous gel | thick viscous gel | thick viscous gel |
| Color | milky white | milky white | milky white |
| Clarity | opaque | opaque | opaque |

EXAMPLES 9-14

Examples 10, 11, and 14 are prepared by hydrating hydroxyethyl cellulose (HEC) over night in deionized water, adding Noveon AA-1 type polymer and stirring for 1 hour to form a gel. Prednisolone acetate or dexamethasone are then dispersed in part of the gel using a homogenizer over a period of 1.5 hours using a small amount of deionized water to wash the homogenizer and adding the water to the dispersion. The dispersion is then added to the gel and stirred for 20 minutes. Then, disodium edetate, sodium bisulfite and sodium sulfate are added in order with 10 minutes of stirring after each addition. Sodium borate is then added followed by 30 minutes of stirring. Then, the gel is sterilized at 121° C. for 20 minutes, brought to room temperature, and the pH is adjusted to 8.0 by adding 10N sodium hydroxide. Tobramycin is dissolved in water, added to the formulation by sterile filtering through a 0.2 micron filter, and stirred for 20 minutes. The pH is adjusted to 8.7 by adding 10N sodium hydroxide. The final formulation batch size is 150 grams adjusted with water.

Examples 9 and 13 are prepared as described in Example 10 except that HPMC is wetted in hot water (90° C.) until smooth paste is obtained. The remainder of the water is added as very cold water. Example 12 is prepared as in Example 10 except that no HEC is added. Example 12 is prepared as in Example 10 except that no HEC is added.

TABLE 8

Formulations and Various Properties of Examples 9-14

| INGREDIENTS | Ex. 9 % w/w | Ex. 10 % w/w | Ex. 11 % w/w | Ex. 12 % w/w | Ex. 13 % w/w | Ex. 14 % w/w |
|---|---|---|---|---|---|---|
| Noveon TM AA-1 | 1.0 | 1.0 | 1.0 | 1.0 | 1.0 | 1.0 |
| Hydroxypropylmethyl Cellulose, USP | 0.2 | — | — | — | 0.2 | — |
| Hydroxyethyl Cellulose, USP | — | 0.2 | 0.2 | — | — | 1.0 |
| Disodium Edetate USP | 0.1 | 0.1 | 0.1 | 0.1 | 0.1 | 0.1 |
| Sodium Bisulfite | 0.1 | 0.1 | — | 0.1 | — | — |
| Sodium Sulfate, USP | 0.05 | 0.05 | 0.05 | 0.05 | 0.05 | 0.05 |
| Sodium Borate, NF | 1.5 | 1.5 | 1.5 | 1.5 | 1.5 | 1.5 |
| Tobramycin, USP | 0.33 | 0.33 | 0.33 | 0.33 | 0.33 | 0.33 |
| Prednisolone Acetate, USP | 0.6 | 0.6 | — | 0.6 | — | — |
| Dexamethasone, USP | — | — | 0.1 | — | 0.1 | 0.1 |
| Water for injection, q.s. | 100 | 100 | 100 | 100 | 100 | 100 |
| pH | 8.7 | 8.7 | 8.8 | 8.8 | 8.8 | 8.7 |
| Osm., mOsm/Kg | 238 | 238 | 217 | 237 | 213 | 223 |
| Viscosity, (CP-52, 1.5 rpm) | 16600 | 8750 | 9150 | 7550 | 16,000 | 6810 |
| Appearance | thick viscous gel | thick viscous gel | thick viscous gel | thick viscous gel | thick viscous gel | thick viscous gel |
| Color | milky white | milky white | colorless | milky white | colorless | colorless |
| Clarity | opaque | opaque | opaque | opaque | opaque | opaque |
| Batch size, gm | 150 | 150 | 150 | 150 | 150 | 150 |
| Sterile | Yes | Yes | Yes | Yes | Yes | Yes |

EXAMPLE 15

A preferred formulation is prepared as described in Examples 10. The amount of each component in the formulation is set forth in Table 9.

TABLE 9

| Amount of Each Component and Formulation | Percent (W/W) |
|---|---|
| Noveon TM AA-1 | 1.00 |
| Hydroxyethyl cellulose | 0.20 |
| Disodium Edetate | 0.10 |
| Sodium Sulfate | 0.05 |
| Sodium Borate | 1.50 |
| Sodium Bisulfite | 0.1 |
| Prednisolone Acetate | 0.6 |
| Tobramycin | 0.3 |
| Deionized Water, q.s. | 100.00 |
| pH | 8.8 |
| Viscosity, cps | 14,000 |
| Osmolarity, mOsm/Kg | 240 |
| Particle Size Distribution | 100% <20 microns |

The above discussion of this invention is directed primarily to preferred embodiments and practices thereof. It will be readily apparent to those skilled in the art that further changes and modifications in actual implementation of the concepts described herein can easily be made without departing from the spirit and scope of the invention as defined by the following claims.

We claim:

1. A sustained release topical ophthalmic medicament delivery system, comprising:
   an aqueous ophthalmic gel suspension at a pH equal to or greater than about 7.5 and an osmotic pressure of from about 10 to about 400 mOsM containing a pharmaceutically effective amount of one or more ophthalmic medicaments, at least one of the medicaments having multiple amine groups, and from about 0.05% to about 10.0% by weight, based on the total weight of the suspension, of a lightly cross-linked carboxyl-containing polymer with less than about 5% by weight of a cross-linking agent, such weight percentage being based on the total weight of monomers polymerized, said suspension having a viscosity of from about 1,000 to about 100,000 centipoises prior to administration to the eye and being administrable to the eye in drop or ribbon form, said polymer having an average particle size of not more than about 50 μm in equivalent spherical diameter, wherein, upon contact of the suspension with the tear fluid of the eye, the suspension remains a gel in the eye for a prolonged period of time allowing for the sustained release of the one or more medicaments contained therein.

2. The sustained release topical ophthalmic medicament delivery system as defined by claim 1, wherein the medicament containing multiple amine groups is an antibiotic.

3. The sustained release topical ophthalmic medicament delivery system as defined by claim 2, wherein the antibiotic is selected from the group consisting of emilorde, tetracycline, chlortetracycline, bacitracin, amikacin, neomycin, polymycin, polymycin B, gramicidin, oxytetracycline, chloramphenicol, gentamycin, penicillins, erythromycin, sulfacetamide, tobramycin, trospectomycin, vancomycin, enoracin and clindamycin.

4. The sustained release topical ophthalmic medicament delivery system as defined by claim 2, wherein said antibiotic is tobramycin.

5. The sustained release topical ophthalmic medicament delivery system as defined by claim 3, wherein the pH is greater than about 8.0 or greater.

6. The sustained release topical ophthalmic medicament delivery system as defined in claim 4, wherein the pH is between about 8.4 to about 9.3.

7. The sustained release topical ophthalmic medicament delivery system as defined by claim 1, wherein the viscosity is from about 1,000 to about 30,000 centipoises prior to administration to the eye and the system is administrable to the eye in drop form.

8. The sustained release topical ophthalmic medicament delivery system as defined by claim 3, wherein said viscosity remains from about 5,000 to about 30,000 centipoises after administration to the eye.

9. The sustained release topical ophthalmic medicament delivery system as defined by claim 6, wherein said viscosity remains from about 5,000 to about 15,000 centipoises after administration to the eye.

10. The sustained release topical ophthalmic medicament delivery system as defined by claim 1, wherein the aqueous ophthalmic gel suspension also contains a corticosteroid medicament.

11. The sustained release topical ophthalmic medicament delivery system as defined in claim 3 wherein the aqueous ophthalmic gel suspension also contains a corticosteroidal medicament.

12. The sustained release medicament system of claim 1 wherein the aqueous ophthalmic gel suspension also contains an antiinflammatory agent.

13. The sustained release medicament delivery system of claim 12 wherein the antiinflammatory agent is selected from the group consisting of ibuprofen, diclofenac, flurbiprofen, napoxen, esers of ibuprofen, naproxen, ketorolac, suprofen, interferons and IL1-ra.

14. The sustained release topical ophthalmic medicament delivery system as defined by claim 11, wherein said corticosteroid is selected from the group consisting of fluorometholone, dexamethasone, hydrocortisone, fluorocinolone, medrysone, prednisolone, prednisolone acetate, and methylprednisolone.

15. The sustained release topical ophthalmic delivery system as defined by claim 4 wherein the aqueous ophthalmic gel suspension also contains prednisolone.

16. A sustained release topical ophthalmic medicament delivery system, comprising:

an aqueous ophthalmic gel suspension at a pH equal to or greater than 7.5 and an osmotic pressure of from about 10 to about 400 mOsM containing a pharmaceutically effective amount of an antibiotic and an antiinflammatory agent, at least one of the antibiotic or antiinflammatory agents having multiple amine groups, and from about 0.05% to about 10.0% by weight, based on the total weight of the suspension, of a carboxyl-containing polymer prepared by polymerizing one or more carboxyl-containing monoethylenically unsaturated monomers and less than about 5% by weight of a cross-linking agent, such weight percentages of monomers being based on the total weight of monomers polymerized, said suspension having a viscosity of from about 1,000 to about 100,000 centipoises prior to administration to the eye and being administrable to the eye in drop or ribbon form, said polymer having an average particle size of not more than about 50 μm in equivalent spherical diameter, wherein, upon contact of the suspension with the tear fluid of the eye, the suspension remains a gel in the eye for a prolonged period of time allowing for the sustained release of both the tobramycin and the prednisolone contained therein.

17. The sustained release topical ophthalmic medicament delivery system as defined in claim 16 wherein the aqueous ophthalmic gel contains tobramycin and prednisolone acetate.

18. The sustained released topical ophthalmic medicament delivery system of claim 16 wherein the viscosity is from about 5,000 to about 30,000 centipoises.

* * * * *